United States Patent [19]

Alpern et al.

[11] Patent Number: 5,284,293
[45] Date of Patent: Feb. 8, 1994

[54] DISPENSER BOX FOR PACKAGES OF STERILE SUTURES

[75] Inventors: Marvin Alpern, Glen Ridge, N.J.; Robert J. Cerwin, Pippersville, Pa.; Mario De Martin, Flemington, N.J.; Teresa M. Simons, Milltown, N.J.; Deborah M. Transue, Bridgewater, N.J.

[73] Assignee: Ethicon, Inc., Somerville, N.J.

[21] Appl. No.: 6,575

[22] Filed: Jan. 21, 1993

[51] Int. Cl.$^5$ .............................................. B65D 5/72
[52] U.S. Cl. .................... 229/122.1; 206/63.3; 229/141
[58] Field of Search ............. 229/122.1, 122, 141, 229/147, 149; 206/63.3

[56] References Cited

U.S. PATENT DOCUMENTS

| | | | |
|---|---|---|---|
| 2,288,739 | 7/1942 | Peters | 229/149 X |
| 2,344,008 | 3/1944 | Tragman | 229/147 X |
| 3,164,298 | 1/1965 | Repko | 229/122.1 X |
| 3,580,472 | 5/1971 | Stawski | 229/122.1 |
| 4,405,044 | 9/1983 | Flower et al. | 229/122.1 X |
| 4,574,957 | 3/1986 | Stead | 206/63.3 |
| 4,890,789 | 1/1990 | Lo Duca | 229/185 X |
| 5,048,678 | 9/1991 | Chambers | 206/63.3 |
| 5,121,876 | 6/1992 | Johnson | 229/149 X |

FOREIGN PATENT DOCUMENTS 0373746 6/1990 European Pat. Off. ......... 229/122.1

Primary Examiner—Gary E. Elkins
Assistant Examiner—Christopher McDonald
Attorney, Agent, or Firm—Robert L. Minier

[57] ABSTRACT

An improved dispenser box for suture packages. The dispenser is stable and will dispense single or plural packages.

2 Claims, 4 Drawing Sheets

DISPENSER BOX FOR PACKAGES OF STERILE SUTURES

FIELD OF INVENTION

The present invention relates to an improved dispenser box and more particularly to a new and improved dispenser box for packages of sterile suture materials and related surgical items.

BACKGROUND OF THE INVENTION

Suture materials are generally packaged in a sterile manner in a foil or a combination of foil and film, foil and paper, paper and film and the like. The sutures may be packaged as single sutures or as a plurality of sutures and they may packaged with or without needles attached. Dispensers for such suture materials or similar packages are well known. One dispenser which has gained wide acceptance for dispensing suture packages is described in U.S. Pat. No. 4,405,044. While this dispenser has wide acceptance, its design has not lent itself to automatic carton making and, hence, has been somewhat costly.

It is an object of the present invention to provide a suture package dispenser that allows for verification of the quantity of suture packages in the box. It is a further object to provide a dispenser that is constructed in a stable manner and minimizes the amount of the dust or other contaminants that may accumulate on the packages in the dispenser. It is an object of the present invention to provide a dispenser that may be produced by automatic equipment. It is a further object of the present invention to reduce the cost of providing suture package dispensers.

SUMMARY OF THE PRESENT INVENTION

The improved dispenser for a plurality of packages for suture material comprises a top panel and a bottom panel. The top and bottom panels are connected together by a pair of side panels. Each of the side panels has a foldable panel attached to an edge of the side panel and extending from the top panel to the bottom panel. These foldable panels are folded over one another and adhered or glued together to form the back panel of the dispenser. A front panel member is attached to an opposite edge of one of the side panels. Attached to the free edge of the front panel member is a foldable tab portion. This foldable tab portion is adhered to the outside of the other side panel to form the front panel of the dispenser. This foldable tab portion is slightly longer than the side panel. In some embodiments of the present invention, the foldable tab portion will extend beyond either the top panel or the bottom panel while in other embodiments it will extend beyond both the top panel and bottom panel. The extended length of the foldable tab portion aids in stabilizing the container when the tab portion is unattached from the side panel and inserted inside the side panel. In a preferred embodiment of the dispenser of the present invention the foldable tab portion extends beyond the bottom edge of the side panel. The bottom panel has a slit therein so that when the tab portion is unattached from said side panel, for example, to refill the container with suture packages, the foldable tab portion may then be inserted inside the side panel with the extending portion being caught or inserted in the slit in the bottom panel to stabilize the front panel.

An opening is disposed at the bottom of the front panel abutting the bottom panel for removing a single package of suture material from the dispenser. An area of the front panel adjacent the opening is easily deflectable to allow for the removal of a plurality of suture packages from the dispenser when desired. In a preferred embodiment of the present invention, a viewing means is dispensed in the front panel. The viewing means is an opening disposed vertically in the front panel and extending at least one fifth the distance between the top and bottom panels to allow for ready determination of the amount of packages of suture materials remaining in the dispenser.

DETAILED DESCRIPTION OF THE DRAWINGS

Figure 1:
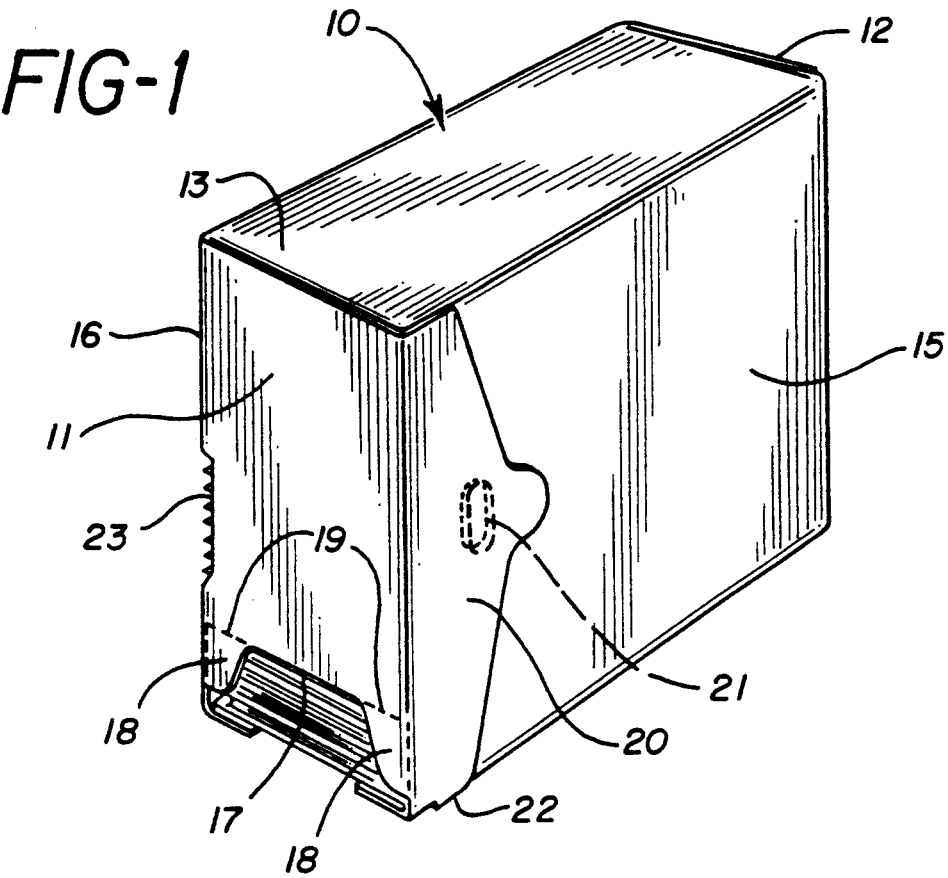
FIG. 1 is a perspective view from the front of a dispenser in accordance with the present invention.
Figure 2:
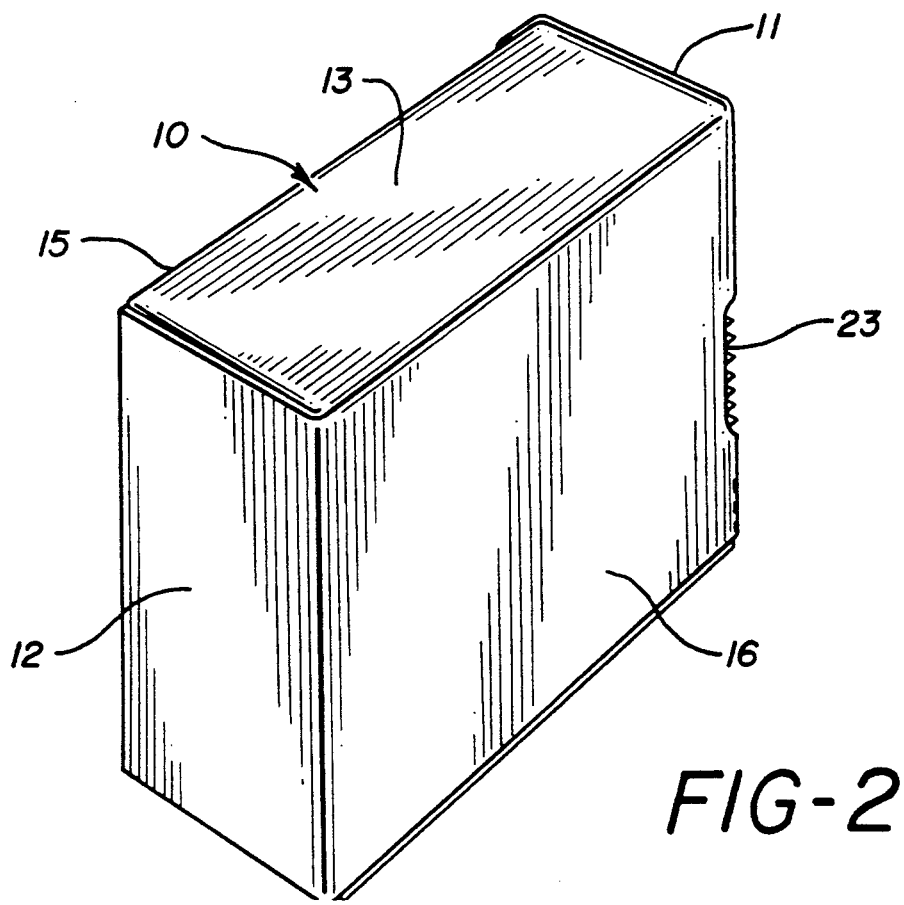
FIG. 2 is a perspective view from the rear of the dispenser depicted in FIG. 1.

Referring to FIGS. 1 and 2 of the drawings, there is shown an improved dispenser of the present invention. The dispenser 10 has a front panel 11, a corresponding rear or back panel 12, a top panel 13, a corresponding bottom panel and a pair of side panels 15 and 16. An opening 17 is disposed at the bottom of the front panel abutting the bottom panel. Adjacent this opening is a deflectable area 18. Actually, it is a pair of deflectable areas with each deflectable area attached to the remainder of the front panel by a score line 19. The front panel includes a foldable tab portion 20 which extends over the side panel and is adhered thereto by glue 21. In this embodiment, the foldable tab portion includes an extending portion 22 that extends slightly below the bottom panel of the dispenser. An opening 23 is disposed along the left hand edge where the front panel and side panel meet. This opening is to view the amount of packages remaining in the dispenser.

Figure 3:
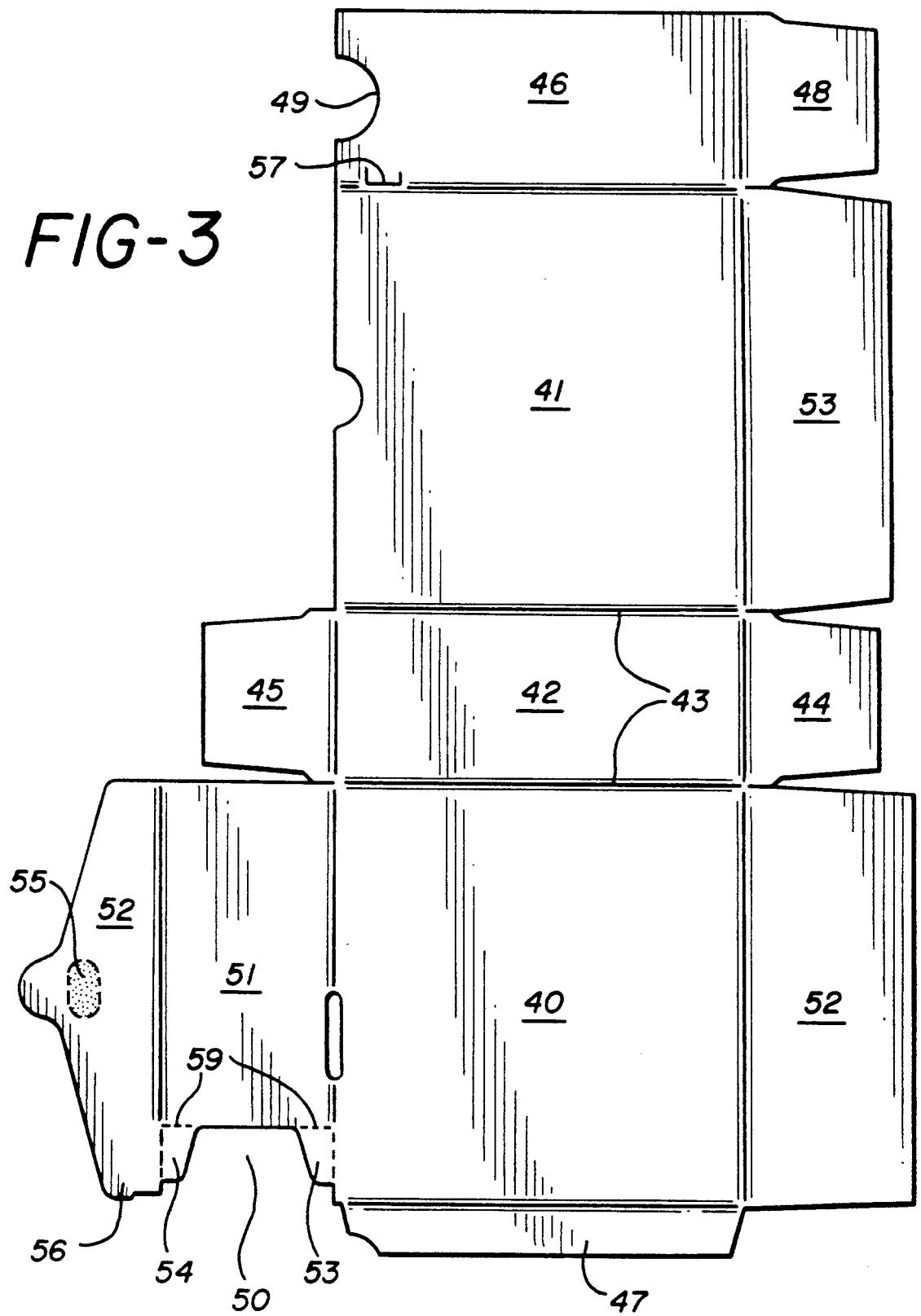
FIG. 3 is a plan view of a blank used to make the dispenser of the present invention.

In FIG. 3 there is depicted a blank from which a dispenser according to the present invention may be automatically produced by automated equipment. The blank comprises a first side panel 40 and a second side panel 41. The side panels are connected together by the top panel 42 which is connected to each side panel by the foldable lines 43. Extending from the top panel on each side thereof are a pair of foldable tabs 44 and 45 to provide stability to the completed dispenser. Extending from one side of the second side panel is the bottom panel 46 and extending from the other or first side panel is a foldable tab portion 47. This tab portion is glued to the bottom panel to form the two side panels connected by the top and bottom panels. If desired, the bottom panel may also include a foldable tab 48 extending from one side thereof to provide further stability to the box dispenser. In the embodiment shown, the opposite edge of the bottom panel has a cutout portion 49 which cooperates with the cutout portion 50 at the bottom of the front panel 51 for easy access to the suture packages in the box. At the back of the first and second side panels are foldable portions 52 and 53 which, when folded inwardly, overlap each other and may be glued together to form the back panel of the dispenser. On the first side panel 40 opposite the back panel portion 52 is the front panel member. This member includes the front panel 51 attached to the side panel and a foldable tab portion 52 attached to the opposite edge of the front panel. At the bottom portion there is the opening 50 and there is a scored line 59 to produce a pair of deflectable portions 53 and 54 at the bottom of the front panel. The foldable tab portion of the front panel may be folded over and adhered 55 to the side panel to form the complete dispenser. The foldable tab portion is slightly longer by virtue of the extension 56, than the side panel. There is a slit 57 in the bottom panel to accept this extended portion once the dispenser has been reopened, refilled, and closed. On pushing the foldable tab portion inside the side panel the extending portion fits into the slit and aids in stabilizing the front of the box.

Figure 4:
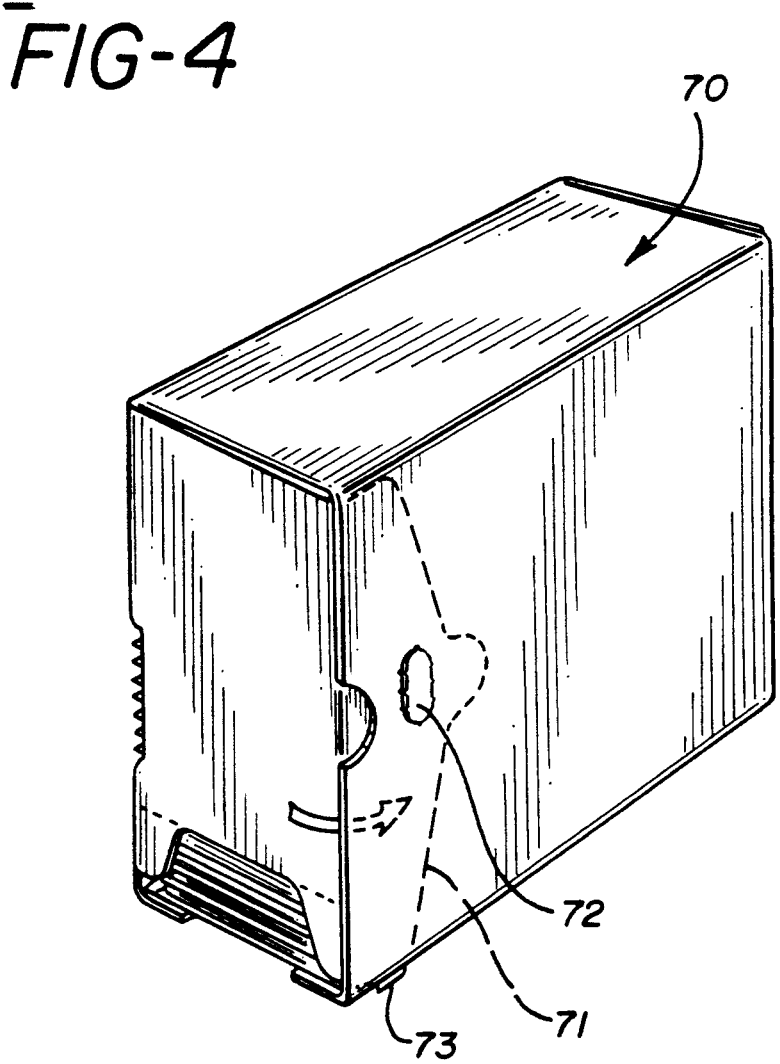
FIG. 4 is a perspective view of a dispenser of the present invention that has been refilled.
Figure 5:
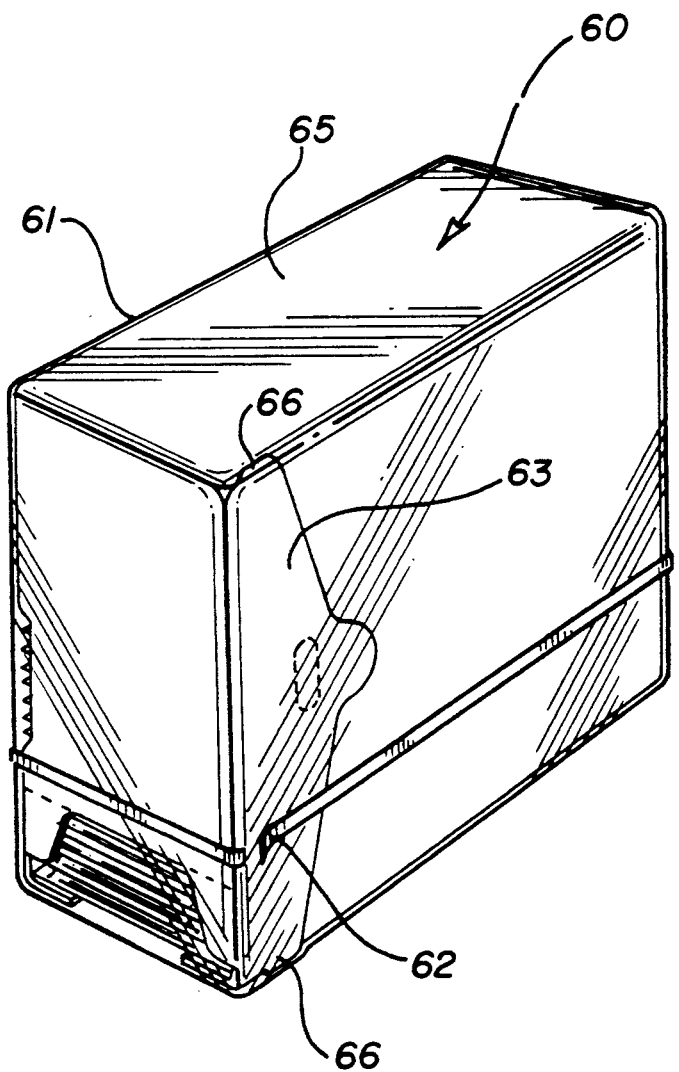
FIG. 5 is a perspective view of a dispenser of the present invention with a film dust cover about the entire dispenser.

As shown in FIG. 4, to refill the dispenser 70 with suture packages it is a simple matter to tear the tab portion 71 away from the side panel at the glue spot 72. The panel at the front of the dispenser is then opened and the dispenser refilled with appropriate suture packages. The tab portion is then reinserted in the side panel with the extending portion 73 of the tab fitting into the slit in the bottom panel to stabilize the front of the box.

When the dispenser blank is automatically folded and glued and then filled to form the dispenser depicted in FIG. 51, the entire package 60 may be enclosed in a transparent film 61. In this embodiment of the dispenser, the foldable tab portion 63 extends beyond the top panel 65 at the extended portion 66. The foldable tab portion also extends beyond the bottom panel at the extended portion 67. Film such as cellophane to keep the package clean during transportation storage etc. is used to enclose the package. When the package is to be used, the tear strip 62 may be removed and the bottom portion of the film wrap discarded. The top portion of the film may either be removed or allowed to remain on the dispenser to assist in maintaining the dispenser dust free. To refill the dispenser, the top portion of the film is removed and the foldable tab portion unglued from the side panel. The dispenser is opened and refilled and the foldable tab portion reinserted in the side panel. The extended portions cause a very tight fit to stabilize the dispenser. If desired, the top portion of the film may be replaced on the top of the dispenser.

It should be noted that it is preferred that when the tab portion is torn open, that either the side panel or the tab portion delaminate and adhere to the adhesive so that there is no sticky adhesive available. A sticky area on the tab portion could disrupt the ready removal of suture packages from the dispenser.

The dispensers of the present invention are preferably made from paper board materials, such as bleached board. These materials are easily formed and can be readily perforated or scored and also are suitable for automation. The glue used may be any of the standard types used to glue paper board materials together. The dust covers may be made from any suitable transparent and flexible film.

Having now described the present invention, it will be readily apparent to those skilled in the art that many variations and modifications may be made without departing from the spirit and scope of the invention.

What is claimed is:

1. A dispenser for a plurality of packages of sterile suture materials, said dispenser comprising:
    a top panel and a bottom panel, one of said top or bottom panels having a slit therein;
    a pair of side panels extending from said top panel to said bottom panel,
    a back panel extending from said top panel to said bottom panel and connecting said side panels, and
    a front panel member having a pair of parallel side edges, one of said edges of said front panel being a side panel and the opposite edge of said front panel having a foldable tab portion extending from said opposite edge, said foldable tab portion being slightly longer than said side panel and being adhered to said side panel to form the front panel of the dispenser, whereby when said tab portion is unadhered from said side panel it may be inserted inside said side panel with said longer portion inserted in the slit to stabilize said front panel, said front panel having an opening disposed at the bottom thereof, said opening abutting the bottom panel for removing a single suture package from said dispenser and an area of said front panel adjacent said opening being easily deflected to allow for removal of a plurality of suture packages at one time.

2. The dispenser according to claim 1 wherein the back panel is formed by a pair of foldable panels, one of said foldable panels being attached to one side panel and the other foldable panel being attached to the other side panel, said foldable panels overlying each other and being adhered together, an opening disposed at the bottom of the front panel and abutting the bottom panel for removing a single suture package from the dispenser, an area of said front panel adjacent said opening being easily deflectable to allow for removal of a plurality of suture packages at one time and viewing means disposed vertically in the front panel adjacent one edge where the front panel meets the side panel to allow for ready determination of the amount of packages remaining in said dispenser.

* * * * *